(12) United States Patent
Ando

(10) Patent No.: US 9,540,541 B2
(45) Date of Patent: *Jan. 10, 2017

(54) ORGANOPOLYSILOXANE EMULSION COMPOSITION

(71) Applicant: SHIN-ETSU CHEMICAL CO., LTD., Tokyo (JP)

(72) Inventor: Yuji Ando, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 31 days.

This patent is subject to a terminal disclaimer.

(21) Appl. No.: 14/378,400

(22) PCT Filed: Mar. 28, 2013

(86) PCT No.: PCT/JP2013/059197
§ 371 (c)(1),
(2) Date: Aug. 13, 2014

(87) PCT Pub. No.: WO2013/161500
PCT Pub. Date: Oct. 31, 2013

(65) Prior Publication Data
US 2015/0037272 A1 Feb. 5, 2015

(30) Foreign Application Priority Data

Apr. 25, 2012 (JP) ................. 2012-099364

(51) Int. Cl.
| | | |
|---|---|---|
| *A61K 8/04* | (2006.01) | |
| *C09D 183/06* | (2006.01) | |
| *C08L 71/02* | (2006.01) | |
| *A61K 8/06* | (2006.01) | |
| *A61K 8/891* | (2006.01) | |
| *A61Q 5/02* | (2006.01) | |
| *A61Q 5/12* | (2006.01) | |
| *C08L 83/04* | (2006.01) | |
| *C08G 77/16* | (2006.01) | |
| *C08G 77/18* | (2006.01) | |

(52) U.S. Cl.
CPC ............. *C09D 183/06* (2013.01); *A61K 8/06* (2013.01); *A61K 8/891* (2013.01); *A61Q 5/02* (2013.01); *A61Q 5/12* (2013.01); *C08L 71/02* (2013.01); *C08L 83/04* (2013.01); *A61K 2800/10* (2013.01); *C08G 77/16* (2013.01); *C08G 77/18* (2013.01); *C08G 2650/58* (2013.01)

(58) Field of Classification Search
None
See application file for complete search history.

(56) References Cited

U.S. PATENT DOCUMENTS 5,661,215 A * 8/1997 Gee .................. C08G 77/06
524/837
2006/0130990 A1 6/2006 Arfaoui et al.
2007/0276087 A1 11/2007 Paul

FOREIGN PATENT DOCUMENTS

| | | | |
|---|---|---|---|
| BE | WO 2012119916 A1 * | 9/2012 | ............. A61K 8/062 |
| JP | 34-002041 B | 4/1959 | |
| JP | 41-013995 B | 8/1966 | |
| JP | 4-178429 A | 6/1992 | |
| JP | 3145394 B2 | 3/2001 | |
| JP | 2002-020490 A | 1/2002 | |
| JP | 2003-252994 A | 9/2003 | |
| JP | 2006-104086 A | 4/2006 | |
| JP | 2006-104267 A | 4/2006 | |
| JP | 2006-282518 A | 10/2006 | |
| JP | 2006-282519 A | 10/2006 | |
| JP | 2008-528775 A | 7/2008 | |

OTHER PUBLICATIONS

International Search Report issued in PCT/JP2013/059197, mailed on May 21, 2013.
Written Opinion issued in PCT/JP2013/059197, mailed on May 21, 2013.
Extended European Search Report dated Dec. 7, 2015 for European Application No. 13782630.1.

* cited by examiner

*Primary Examiner* — Robert A Wax
*Assistant Examiner* — Melissa Mercier
(74) *Attorney, Agent, or Firm* — Birch, Stewart, Kolasch & Birch, LLP

(57) ABSTRACT

An organopolysiloxane emulsion composition produced by the emulsion polymerization of an emulsion that comprises (A) an organopolysiloxane containing a silanol group or an organooxy group, (B) a nonionic surfactant represented by formula (2): $R^2O(EO)_a(PO)_bR^3$ (wherein $R^2$ represents an alkyl group or $R^4(CO)$—; $R^4$ represents an alkyl group; $R^3$ represents an alkyl group or $R^5(CO)$—; $R^5$ represents an alkyl group; EO represents an ethylene oxide group; PO represents an alkylene oxide group; and a and b independently represent 0 to 100, wherein a+b>0 and the sequence of EO and PO may be random or in the form of a block) and (C) a surfactant other than the component (B), and may additionally comprise (D) a polymerization catalyst and (E) water if required. According to the present invention, it becomes possible to produce an extremely stable organopolysiloxane emulsion composition without inhibiting polymerization during the emulsion polymerization of an organopolysiloxane having condensation reactivity. Further, it also becomes possible to reduce the amount of octamethylcyclotetrasiloxane produced during the emulsion polymerization.

9 Claims, No Drawings

ORGANOPOLYSILOXANE EMULSION COMPOSITION

TECHNICAL FIELD

This invention relates to a stable organopolysiloxane emulsion composition obtained from emulsion polymerization of an organopolysiloxane containing a silanol group or organoxy group such as alkoxy capable of condensation reaction.

BACKGROUND ART

In a variety of fields including cosmetics, household agents and parting agents, it is required that an organopolysiloxane having a high degree of polymerization or organopolysiloxane having a branched silicone chain be available in emulsion form. However, when such organopolysiloxane is directly emulsified, a particle size of several microns becomes the limit. So studies were made on the preparation method via emulsion polymerization. For example, it is known from Patent Documents 1 and 2: JP-B S34-2041 and JP-B S41-13995 that cyclic siloxane oligomers are emulsified before emulsion polymerization is conducted in the presence of strong acids or strong bases.

Recently, octamethylcyclotetrasiloxane becomes a matter of concern as environmental loading substance. Samples having a reduced content of octamethylcyclotetrasiloxane are required. It is known that the siloxanes in the above-cited patent documents contain 40,000 ppm or more of octamethylcyclotetrasiloxane. Studies have been made on the method of suppressing the amount of octamethylcyclotetrasiloxane formed.

As one exemplary method, it is known from Patent Document 3: JP 3145394 that a condensation reactive organopolysiloxane having a silanol group at the end of the molecular chain and containing up to 5,000 ppm of a non-condensation reactive organosiloxane oligomer of up to 20 silicon atoms is subjected to emulsion polymerization at 40° C. or lower for a polymerization time within 40 hours. However, an ordinary nonionic surfactant of the structure having a hydroxyl group at the end, which is used to enhance the stability of emulsion, inhibits condensation of silanol. Even after emulsion polymerization is continued for 40 hours, the ultimate viscosity is several million mm²/s. The emulsion polymerization time must be further prolonged before a higher degree of polymerization can be reached.

CITATION LIST

Patent Documents

Patent Document 1: JP-B S34-2041
Patent Document 2: JP-B S41-13995
Patent Document 3: JP 3145394

SUMMARY OF INVENTION

Technical Problem

An object of the invention, which has been made to overcome the above and other problems of the prior art, is to provide an organopolysiloxane emulsion composition in which emulsion polymerization of an organopolysiloxane having a condensation reactive silanol group or organoxy group such as alkoxy readily takes place to the desired degree of polymerization without a risk of inhibitory polymerization as do prior art nonionic surfactants, the composition having improved stability.

Solution to Problem

Making extensive investigations to attain the above object, the inventor has found that when an organopolysiloxane having a condensation reactive silanol group or organoxy group such as alkoxy is subjected to emulsion polymerization in the presence of a nonionic surfactant whose terminal hydroxyl group is blocked with an organic group such as alkyl or acyl, rather than a prior art nonionic surfactant terminated with a hydroxyl group, the reaction takes place to the desired degree of polymerization within a relatively short time without a risk of inhibitory polymerization, and so a highly stable organopolysiloxane emulsion composition is available. The invention is predicated on this finding.

Accordingly, the invention provides an organopolysiloxane emulsion composition as defined below.

[1] An organopolysiloxane emulsion composition obtained from emulsion polymerization of an emulsion comprising (A) 100 parts by weight of an organopolysiloxane containing a silanol or organoxy group, (B) 1 to 100 parts by weight of a nonionic surfactant having the general formula (2):

$$R^2O(EO)_a(PO)_bR^3 \quad (2)$$

wherein $R^2$ is a straight or branched alkyl group of 1 to 30 carbon atoms or an organic group of $R^4(CO)$—, $R^4$ is a straight or branched alkyl group of 1 to 30 carbon atoms, $R^3$ is a straight or branched alkyl group of 1 to 30 carbon atoms or an organic group of $R^5(CO)$—, $R^5$ is a straight or branched alkyl group of 1 to 30 carbon atoms, EO is an ethylene oxide group, PO is an alkylene oxide group of at least 3 carbon atoms, a and b each are a number of 0 to 100, a+b>0, and the sequence of EO and PO may be random or in blocks, (C) 1 to 100 parts by weight of a surfactant other than component (B), (D) 0 to 100 parts by weight of a polymerization catalyst, and (E) 1 to 100,000 parts by weight of water.

[2] The organopolysiloxane emulsion composition of [1] wherein the organopolysiloxane containing a silanol or organoxy group (A) is an organopolysiloxane having the general formula (1):

$$R^0O(R^1{}_2SiO)_nR^0 \quad (1)$$

wherein $R^0$ is independently hydrogen or a substituted or unsubstituted monovalent hydrocarbon group of 1 to 20 carbon atoms, $R^1$ is independently a substituted or unsubstituted monovalent hydrocarbon group of 1 to 20 carbon atoms, and n is such a number that the organopolysiloxane may have a viscosity of 20 to 100,000 me/s at 25° C.

[3] The organopolysiloxane emulsion composition of [1] or [2] wherein component (C) is an anionic surfactant.

[4] The organopolysiloxane emulsion composition of any one of [1] to [3] wherein the organopolysiloxane in the emulsion composition contains up to 4,000 ppm of octamethylcyclotetrasiloxane.

Advantageous Effects of Invention

As opposed to prior art nonionic surfactants terminated with a hydroxyl group, which inhibit emulsion polymerization of an organopolysiloxane having condensation reactivity, the invention uses a nonionic surfactant whose terminal hydroxyl is blocked with an organic group such as alkyl or acyl and enables to produce a highly stable organopolysiloxane emulsion composition without inhibiting polymerization. Further, the invention can reduce the amount of octamethylcyclotetrasiloxane formed in the course of emulsion polymerization.

DESCRIPTION OF EMBODIMENTS

The invention is directed to an organopolysiloxane emulsion composition obtained from emulsion polymerization of an emulsion comprising (A) an organopolysiloxane containing a silanol or organoxy group, (B) a nonionic surfactant having the general formula (2):

wherein $R^2$ is a straight or branched alkyl group of 1 to 30 carbon atoms or an organic group of $R^4(CO)-$, $R^4$ is a straight or branched alkyl group of 1 to 30 carbon atoms, $R^3$ is a straight or branched alkyl group of 1 to 30 carbon atoms or an organic group of $R^5(CO)-$, $R^5$ is a straight or branched alkyl group of 1 to 30 carbon atoms, EO is an ethylene oxide group, PO is an alkylene oxide group of at least 3 carbon atoms, a and b each are a number of 0 to 100, a+b>0, and the sequence of EO and PO may be random or in blocks, (C) a surfactant other than component (B), (D) a polymerization catalyst, which is optional if component (C) is catalytic, and (E) water.

Component (A) is an organopolysiloxane containing a condensation reactive silanol group or organoxy group such as alkoxy. It is capable of condensation reaction under acidic or basic conditions.

Examples of the condensation reactive alkoxy group include methoxy, ethoxy, isopropoxy, n-propoxy, t-butoxy, s-butoxy, and n-butoxy.

Examples of the organopolysiloxane containing a condensation reactive silanol group or organoxy group such as alkoxy include those organopolysiloxanes having the general formula (1):

$$R^0O(R^1{}_2SiO)_nR^0 \quad (1)$$

wherein $R^1$ is independently hydrogen or a substituted or unsubstituted monovalent hydrocarbon group of 1 to 20 carbon atoms, $R^1$ is independently a substituted or unsubstituted monovalent hydrocarbon group of 1 to 20 carbon atoms, and n is such a number that the organopolysiloxane may have a viscosity of 20 to 100,000 me/s at 25° C.

When $R^0$ is hydrogen, the organopolysiloxane of formula (1) is terminated with a hydroxyl group (or silanol group). When $R^0$ is a monovalent hydrocarbon group, the organopolysiloxane of formula (1) is terminated with an organoxy group. In the latter case, $R^0$ is preferably a monovalent hydrocarbon group of 1 to 10 carbon atoms, especially 1 to 4 carbon atoms, and specifically alkyl group. Of the organoxy groups represented by $-OR^0$, the above-mentioned groups are preferred.

$R^1$ is independently a substituted or unsubstituted monovalent hydrocarbon group of 1 to 20 carbon atoms, preferably 1 to 10 carbon atoms. Examples include alkyl groups such as methyl, ethyl, propyl, butyl, pentyl, hexyl, heptyl, octyl, nonyl, decyl, dodecyl, tetradecyl, hexadecyl, octadecyl, cyclopentyl, and cyclohexyl; aryl groups such as phenyl, tolyl and naphthyl; alkenyl groups such as vinyl and allyl; aralkyl groups such as benzyl, phenylethyl and phenylpropyl; and substituted forms of the foregoing in which some or all hydrogen atoms are substituted by halogen atoms, or organic groups containing a polar group such as amino, acryloxy, methacryloxy, epoxy, mercapto, carboxyl or hydroxyl. Preferred are monovalent hydrocarbon groups of 1 to 6 carbon atoms, such as methyl, ethyl, propyl, butyl and phenyl. It is more preferred that methyl account for at least 80 mol % of all $R^1$.

The subscript n is such a number that the organopolysiloxane may have a viscosity at 25° C. of 20 to 100,000 mm²/s, preferably 50 to 50,000 mm²/s, and more preferably 50 to 10,000 mm²/s. As long as the viscosity is in a range of 20 to 100,000 mm²/s, the emulsion is fully stable. It is noted that the viscosity is measured by an Ostwald viscometer.

Preferably component (A) is an organopolysiloxane blocked with a silanol group or organoxy group such as alkoxy at the end of its molecular chain. Its molecular structure may be straight or branched.

Component (B) is a nonionic surfactant having the general formula (2).

Herein $R^2$ is a straight or branched alkyl group of 1 to 30 carbon atoms or an organic group of $R^4(CO)-$, wherein $R^4$ is a straight or branched alkyl group of 1 to 30 carbon atoms. $R^3$ is a straight or branched alkyl group of 1 to 30 carbon atoms or an organic group of $R^5(CO)-$, wherein $R^5$ is a straight or branched alkyl group of 1 to 30 carbon atoms. EO is an ethylene oxide group, PO is an alkylene oxide group of at least 3 carbon atoms, such as propylene oxide or butylene oxide, a and b each are a number of 0 to 100, a+b>0. The sequence of EO and PO may be random or in blocks.

Examples of the straight or branched alkyl group of 1 to 30 carbon atoms, represented by $R^2$ to $R^5$, include methyl, ethyl, n-propyl, i-propyl, n-butyl, i-butyl, t-butyl, n-pentyl, 1-methyl-n-butyl, 2-methyl-n-butyl, 3-methyl-n-butyl, 1,1-dimethyl-n-propyl, n-hexyl, 1-methyl-n-pentyl, 2-methyl-n-pentyl, 1,1-dimethyl-n-butyl, 1-ethyl-n-butyl, 1,1,2-trimethyl-n-propyl, n-heptyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosyl.

Of the groups represented by $R^2$ and $R^3$, it is preferred that $R^2$ be a straight or branched alkyl group of 6 to 30 carbon atoms, and $R^3$ be a straight or branched alkyl group of 1 to 5 carbon atoms; more preferably $R^2$ is a straight or branched alkyl group of 10 to 14 carbon atoms, and $R^3$ is a straight or branched alkyl group of 1 to 3 carbon atoms. It is also preferred that $R^2$ be an organic group of $R^4(CO)-$ wherein $R^4$ is a straight or branched alkyl group of 6 to 30 carbon atoms, and $R^3$ be a straight or branched alkyl group of 1 to 5 carbon atoms; more preferably, $R^4$ is a straight or branched alkyl group of 10 to 14 carbon atoms, and $R^3$ is a straight or branched alkyl group of 1 to 3 carbon atoms.

EO is ethylene oxide, and PO is an alkylene oxide of at least 3 carbon atoms. Exemplary alkylene oxides include those of 3 to 8 carbon atoms such as propylene oxide, butylene oxide, pentylene oxide, hexylene oxide, heptylene oxide and octylene oxide. The subscripts a and b each are a number of 0 to 50, and a+b>0. The values of a and b are preferably such that the surfactant may have an HLB in the range of 4 to 18, more preferably 7 to 17. Specifically, a has a value of 2 to 40, more preferably 2 to 30, and b has a value of 0 to 30, more preferably 0 to 20. The sequence of EO and PO may be random or in blocks.

Examples of the nonionic surfactant of formula (2) are shown below.

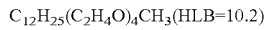

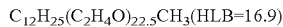

The amount of component (B) used is 1 to 100 parts by weight, preferably 2 to 25 parts by weight, and more preferably 3 to 10 parts by weight per 100 parts by weight of component (A). If the amount of component (B) is too less, it may be difficult to form an O/W type emulsion, or the emulsion tends to lose stability. If the amount of component (B) is too much, the performance of silicone serving as base oil on use of the emulsion can be adversely affected by the emulsifier.

The surfactants as component (B) may be used alone or in admixture of two or more.

Component (C) is a surfactant other than component (B), examples of which include anionic surfactants, cationic surfactants, and nonionic surfactants other than the nonionic surfactants of formula (2).

Specifically, the anionic surfactants are preferably those of the general formula: $R^6OSO_3M$ or $R^6\text{-Ph-}OSO_3M$ wherein $R^6$ is a straight or branched alkyl group of 6 to 30 carbon atoms, Ph is phenyl, and M is hydrogen, metal element or ammonium or quaternary ammonium ion.

Examples of the straight or branched alkyl group of 6 to 30 carbon atoms include n-hexyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosyl. Suitable metal elements include alkali metals such as lithium, sodium, potassium, rubidium and cesium; and alkaline earth metals such as calcium, strontium, barium and radium. Ammonium ions or quaternary ammonium ions such as ammonium salts and triethanolamine salts are also included.

More preferably, $R^6$ is a straight or branched alkyl group of 6 to 12 carbon atoms, and M is hydrogen, an alkali metal element or alkaline earth metal element. Examples include hexylbenzenesulfonic acid, octylbenzenesulfonic acid, decylbenzenesulfonic acid, dodecylbenzenesulfonic acid, cetylbenzenesulfonic acid, and myristylbenzenesulfonic acid, and salts thereof.

Also included are higher fatty acids such as lauric acid, stearic acid, oleic acid and linoleic acid and salts thereof, and sulfuric acid esters of polyoxyethylene monoalkyl ethers represented by the general formula: $R^6O(EO)_c(PO)_dSO_3M$ or $R^6\text{-Ph-}O(EO)_c(PO)_dSO_3M$ wherein $R^6$, M, EO and PO are as defined above, and c and d each are 0 to 100; alkylnaphthylsulfonic acids and salts thereof.

Suitable cationic surfactants include quaternary ammonium hydroxides such as octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, didodecyldimethylammonium hydroxide, dioctadecyldimethylammonium hydroxide, and salts thereof.

Suitable nonionic surfactants other than the nonionic surfactants of formula (2) include polyoxyalkylene alkyl ethers, polyoxyalkylene alkyl phenol ethers, polyoxyalkylene alkyl esters, polyoxyalkylene sorbitan alkyl esters, polyethylene glycol, polypropylene glycol, and diethylene glycol. Of these, preferred are those of the general formula: $R^6O(EO)_e(PO)_fH$ wherein $R^6$ is as defined above, each of e and f is 0 to 100, e+f>0, EO is ethylene oxide, PO is an alkylene oxide of at least 3 carbon atoms such as propylene oxide or butylene oxide, and the sequence of EO and PO may be random or in blocks. It is more preferred that $R^6$ be a straight or branched alkyl group of 6 to 12 carbon atoms, and e and f be 0 to 25. Notably, when a nonionic surfactant is used, it may be added in an amount that does not adversely affect formation of the desired polymer, because the nonionic surfactant is inhibitory to condensation.

Any of the above-listed surfactants may be used as component (C), with anionic surfactants being preferred.

The surfactants as component (C) may be used alone or in admixture of two or more.

The amount of the surfactant used as component (C) is 1 to 100 parts by weight, preferably 2 to 25 parts by weight, and more preferably 3 to 10 parts by weight per 100 parts by weight of component (A). If the amount of component (C) is too less, it may be difficult to form an O/W type emulsion, or the emulsion tends to lose stability. If the amount of component (C) is too much, the performance of silicone serving as base oil on use of the emulsion can be adversely affected by the emulsifier.

Component (D) is a polymerization catalyst which is selected from acidic and basic catalysts. Exemplary acidic catalysts include hydrochloric acid, sulfuric acid, and cation-exchange resins. Exemplary basic catalysts include alkaline metal hydroxides such as sodium hydroxide and potassium hydroxide, and anion-exchange resins. It is noted that component (D) may be omitted if component (C) blended has catalysis, for example, if a compound having a functional group such as —$SO_3H$ or —COOH, which has the function of an acidic catalyst or a compound having $R_4NOH$ (ammonium hydroxide), which has the function of a basic catalyst, is used as component (C).

The amount of component (D) used is 0 to 100 parts by weight, preferably 0 to 20 parts by weight, and if used, at least 0.1 part by weight, especially at least 1 part by weight per 100 parts by weight of component (A). If the amount of component (D) is too less, polymerization may not proceed to a full extent. If the amount of component (D) is excessive, it may become necessary to add a more amount of neutralizing agent, compromising the stability of the emulsion.

Component (E) is water, which is used in an amount of 1 to 100,000 parts by weight, preferably 1 to 1,000 parts by weight, and more preferably 2 to 200 parts by weight, per 100 parts by weight of component (A). If the amount of water is too less, it may be difficult to form an O/W type emulsion. If the amount of water is excessive, the concentration of the catalyst may be reduced so that polymerization may not proceed to a full extent.

The method of conducting emulsion polymerization may be by emulsifying organopolysiloxane as component (A), nonionic surfactant as component (B), surfactant as component (C), and water as component (E) on an emulsifying machine such as a homogenizer, high-pressure homogenizer, homo-disper, homo-mixer, colloidal mill, line mixer, universal mixer, ultra-mixer, planetary mixer, or combined mixer. At this point, the polymerization catalyst as component (D) may be emulsified together with components (A), (B), (C) and (E), or added after components (A), (B), (C) and (E) have been emulsified, while the catalyst may be omitted if component (C) has catalysis. Also, in cases where component (C) has catalysis, or where component (D) is added in the course of emulsification, so that condensation may take place at the same time, it is preferred that emulsification be conducted at a temperature of lower than 40° C. If emulsification is conducted at a temperature of 40° C. or higher, there is a risk that more octamethylcyclotetrasiloxane forms. Thus, emulsification is preferably conducted at a temperature of lower than 15° C., more preferably lower than 5° C.

Also preferably, the polymerization step is conducted at a temperature of lower than 40° C., more preferably lower than 15° C., and even more preferably lower than 5° C. for a time within 48 hours, more preferably within 20 hours. If polymerization is conducted at a temperature in excess of 40° C., there is a risk that more octamethylcyclotetrasiloxane forms.

It is noted that the organopolysiloxane resulting from the above-mentioned emulsion polymerization will reach a viscosity of at least 1,000,000 mPa·s, preferably at least 3,000,000 mPa·s, and more preferably at least 8,000,000 mPa·s within 20 hours.

In the practice of the invention, the organopolysiloxane resulting emulsion polymerization may contain up to 4,000 ppm of octamethylcyclotetrasiloxane. Notably, the content of octamethylcyclotetrasiloxane may be measured by gas chromatography.

Also, prior to the polymerization step, an acid catalyst may be added for the purpose of reducing the polymerization step, or an emulsifier may be added for the purpose of improving the stability of emulsion.

Polymerization is continued until the desired polymer is obtained, whereupon it is interrupted. The polymerization may be interrupted by neutralizing with an alkaline substance such as sodium carbonate, sodium hydroxide, triethanolamine or ammonia, or an acidic substance such as acetic acid, formic acid, phosphoric acid or hydrochloric acid so as to provide a pH value in the range of 4 to 8. At this point, water may be added to adjust the silicone concentration, and an antiseptic, antifungal or similar agent may be added to the emulsion for storage.

To the emulsion after the emulsifying step, emulsion polymerization step or neutralization step, an organopolysiloxane such as $R^7_3SiO(R^7_2SiO)_gSiR^7_3$ may be added to form an organopolysiloxane end-capped with a triorganosilyl group, or an organoxysilane such as $R^7_3Si(OR^8)_1$, $R^7_2Si(OR^8)_2$ or $R^7_1Si(OR^8)_3$ may be added to introduce branched units into the siloxane chain or introduce various functional groups.

In the above formulae, $R^7$ is independently hydrogen or a substituted or unsubstituted monovalent hydrocarbon group of 1 to 20 carbon atoms, with examples of the substituted or unsubstituted monovalent hydrocarbon group being as exemplified above for $R^1$. Preferably $R^7$ is a monovalent hydrocarbon group of 1 to 6 carbon atoms, such as methyl, ethyl, propyl, butyl or phenyl. The subscript g is 0 to 100.

Also, $R^8$ is independently hydrogen or an alkyl group of 1 to 20 carbon atoms. Examples of the alkyl group of 1 to 20 carbon atoms include methyl, ethyl, propyl, butyl, pentyl, hexyl, heptyl, octyl, nonyl, decyl, dodecyl, tetradecyl, hexadecyl, octadecyl, cyclopentyl, and cyclohexyl. $R^8$ is preferably methyl, ethyl or isopropyl.

EXAMPLES

Examples and Comparative Examples are given below for illustrating the invention although the invention is not limited to the Examples below.

The particle size is a median diameter as measured on a volume basis by a laser diffraction/scattering mode particle size distribution analyzer LA-920 (Horiba, Ltd.). Notably the median diameter is a particle diameter corresponding to cumulative 50% when the particle size distribution is expressed as cumulative distribution. On the measurement, a relative refractive index 1.05 (refractive index of dimethylpolysiloxane 1.40, refractive index of water 1.33) was utilized.

The viscosity of siloxane is a viscosity as measured at 25° C. by adding, with stirring, 300 g of isopropyl alcohol to 300 g of the emulsion as prepared, drying only the precipitated dimethylsiloxane at 105° C. for 3 hours, and analyzing by a rotational viscometer.

The content of octamethylcyclotetrasiloxane (D4) is a value which is measured by extracting 0.1 g of the emulsion as prepared with 10 ml of acetone having 20 ppm of tetradecane as internal standard added thereto (shaking for 3 hours), allowing to stand overnight, and quantitatively analyzing the acetone layer by gas chromatography.

With respect to stability, a 100-g glass vial was filled with the emulsion as prepared and allowed to stand at 50° C. for one month, whereupon the outer appearance of the emulsion was observed. Stability was evaluated according to the following criterion.

O: separation into two layers is not confirmed
x: separation into two layers is confirmed Example 1

Using a homo-disper, 2.0 parts by weight of $C_{12}H_{25}O(C_2H_4O)_4CH_3$ (HLB=10.2), 6.0 parts by weight of $C_{12}H_{25}O(C_2H_4O)_{22.5}CH_3$ (HLB=16.9), 4.0 parts by weight of dodecylbenzenesulfonic acid, and 6.0 parts by weight of water were emulsified in 100 parts by weight of an organopolysiloxane capped with a silanol group at the end of its molecular chain and having a viscosity of 5,000 mm²/s. Then 79.6 parts by weight of water was added to the mixture, which was diluted and dispersed by a homo-mixer, whereupon emulsion polymerization was carried out at 0° C. for 20 hours and 48 hours. Thereafter, 2.4 parts by weight of triethanolamine was added for neutralization, yielding an emulsion. The results are shown in Table 1.

Example 2

Using a homo-disper, 1.0 part by weight of $C_{12}H_{25}O(C_2H_4O)_4CH_3$ (HLB=10.2), 3.0 parts by weight of $C_{12}H_{25}O(C_2H_4O)_{22.5}CH_3$ (HLB=16.9), 4.0 parts by weight of dodecylbenzenesulfonic acid, and 6.0 parts by weight of water were emulsified in 100 parts by weight of an organopolysiloxane capped with a silanol group at the end of its molecular chain and having a viscosity of 5,000 mm²/s. Then 84.4 parts by weight of water was added to the mixture, which was diluted and dispersed by a homo-mixer, whereupon emulsion polymerization was carried out at 0° C. for 20 hours and 48 hours. Thereafter, 2.4 parts by weight of triethanolamine was added for neutralization, yielding an emulsion. The results are shown in Table 1.

Comparative Example 1

Using a homo-disper, 2.0 parts by weight of polyoxyethylene (4 mol) lauryl ether, 6.0 parts by weight of polyoxyethylene (23 mol) lauryl ether, 4.0 parts by weight of dodecylbenzenesulfonic acid, and 6.0 parts by weight of water were emulsified in 100 parts by weight of an organopolysiloxane capped with a silanol group at the end of its molecular chain and having a viscosity of 5,000 mm²/s. Then 79.6 parts by weight of water was added to the mixture, which was diluted and dispersed by a homo-mixer, whereupon emulsion polymerization was carried out at 0° C. for 20 hours and 48 hours. Thereafter, 2.4 parts by weight of triethanolamine was added for neutralization, yielding an emulsion. The results are shown in Table 1. The organopolysiloxane in the emulsion had a low viscosity as compared with Example 1, indicating inhibited condensation.

Comparative Example 2

Using a homo-disper, 1.0 part by weight of polyoxyethylene (4 mol) lauryl ether, 3.0 parts by weight of polyoxyethylene (23 mol) lauryl ether, 4.0 parts by weight of dodecylbenzenesulfonic acid, and 6.0 parts by weight of water were emulsified in 100 parts by weight of an organopolysiloxane capped with a silanol group at the end of its molecular chain and having a viscosity of 5,000 mm$^2$/s. Then 84.4 parts by weight of water was added to the mixture, which was diluted and dispersed by a homo-mixer, whereupon emulsion polymerization was carried out at 0° C. for 20 hours and 48 hours. Thereafter, 2.4 parts by weight of triethanolamine was added for neutralization, yielding an emulsion. The results are shown in Table 1. The organopolysiloxane in the emulsion had a low viscosity as compared with Example 2, indicating inhibited condensation.

TABLE 1

| | Condensation time (hr) | Particle size (nm) | Siloxane viscosity (mPa·s) | D4 content (ppm) | Stability @50° C./1 month |
|---|---|---|---|---|---|
| Example 1 | 20 | 140 | 11,000,000 | 1,900 | ○ |
| | 48 | 150 | 48,000,000 | 3,700 | ○ |
| Example 2 | 20 | 210 | 22,000,000 | 1,900 | ○ |
| | 48 | 160 | 95,000,000 | 3,800 | ○ |
| Comparative Example 1 | 20 | 130 | 3,300,000 | 2,100 | ○ |
| | 48 | 140 | 12,000,000 | 4,500 | ○ |
| Comparative Example 2 | 20 | 210 | 7,600,000 | 2,300 | ○ |
| | 48 | 200 | 20,000,000 | 4,600 | ○ |

INDUSTRIAL APPLICABILITY

Since the composition of the invention is improved in stability and feeling on use, it is especially useful as cosmetics and household agents, for example, as hair care products such as shampoo and conditioner. The composition can also be utilized as protective members for household tools and goods, parting agents for molds used in processing of rubber products and plastic products, and fabric treating agents for the purpose of imparting water repellency and plasticity to fabrics.

The invention claimed is:

1. An organopolysiloxane emulsion composition obtained from emulsion polymerization of an emulsion comprising
   (A) an organopolysiloxane containing a silanol or organoxy group,
   (B) 1 to 100 parts by weight of a nonionic surfactant having the general formula (2):

$$R^2O(EO)_a(PO)_bR^3 \quad (2)$$

wherein $R^2$ is a straight or branched alkyl group of 1 to 30 carbon atoms or an organic group of $R^4(CO)$—, $R^4$ is a straight or branched alkyl group of 1 to 30 carbon atoms, $R^3$ is a straight or branched alkyl group of 1 to 30 carbon atoms or an organic group of $R^5(CO)$—, $R^5$ is a straight or branched alkyl group of 1 to 30 carbon atoms, EO is an ethylene oxide group, PO is an alkylene oxide group of at least 3 carbon atoms, a and b each are a number of 0 to 100, a+b>0, and the sequence of EO and PO may be random or in blocks,
   (C) 1 to 100 parts by weight of a surfactant other than component (B),
   (D) 0 to 100 parts by weight of a polymerization catalyst, and
   (E) 1 to 100,000 parts by weight of water;
   wherein the amounts are based on 100 parts by weight of the component (A).

2. The organopolysiloxane emulsion composition of claim 1 wherein the organopolysiloxane containing a silanol or organoxy group (A) is an organopolysiloxane having the general formula (1):

$$R^0O(R^1{}_2SiO)_nR^0 \quad (1)$$

wherein $R^0$ is independently hydrogen or a substituted or unsubstituted monovalent hydrocarbon group of 1 to 20 carbon atoms, $R^1$ is independently a substituted or unsubstituted monovalent hydrocarbon group of 1 to 20 carbon atoms, and n is such a number that the organopolysiloxane may have a viscosity of 20 to 100,000 mm$^2$/s at 25° C.

3. The organopolysiloxane emulsion composition of claim 1 or 2 wherein component (C) is an anionic surfactant.

4. The organopolysiloxane emulsion composition of claim 1 wherein the organopolysiloxane in the emulsion composition contains up to 4,000 ppm of octamethylcyclotetrasiloxane.

5. The organopolysiloxane emulsion composition of claim 1, wherein $R^2$ is a straight or branched alkyl group of 6 to 30 carbon atoms, and $R^3$ is a straight or branched alkyl group of 1 to 5 carbon atoms in the general formula (2).

6. The organopolysiloxane emulsion composition of claim 1, wherein $R^2$ is an organic group of $R^4(CO)$—, $R^4$ is a straight or branched alkyl group of 6 to 30 carbon atoms, and $R^3$ is a straight or branched alkyl group of 1 to 5 carbon atoms in the general formula (2).

7. The organopolysiloxane emulsion composition of claim 1, wherein the nonionic surfactant of formula (2) is $C_{12}H_{25}O(C_2H_4O)_4CH_3$ or $C_{12}H_{25}O(C_2H_4O)_{22.5}CH_3$.

8. The organopolysiloxane emulsion composition of claim 1, wherein the organoxy group is an alkoxy group.

9. The organopolysiloxane emulsion composition of claim 1, wherein b is 0 in the general formula (2).

* * * * *